United States Patent [19]

Marion et al.

[11] Patent Number: 6,049,020

[45] Date of Patent: *Apr. 11, 2000

[54] PROCESS FOR PRODUCING AN ETHER AND AN OLEFIN FROM A HYDROCARBON CUT CONTAINING AT LEAST ONE TERTIARY OLEFIN BY SYNTHESISING THEN DECOMPOSING AN ETHER, COMPRISING A FIRST STEP FOR PURIFYING THE OLEFIN BY FRACTIONATION

[75] Inventors: Marie-Claire Marion, Villeurbanne; Vincent Coupard, Lyons; Alain Forestiere, Vernaison; Philippe Travers, Rueil Malmaison; Jean-Charles Viltard, Valence, all of France

[73] Assignee: Institut Francais du Petrole, Rueil Malmaison Cedex, France

[*] Notice: This patent is subject to a terminal disclaimer.

[21] Appl. No.: 09/052,977

[22] Filed: Apr. 1, 1998

[30] Foreign Application Priority Data

Apr. 2, 1997 [FR] France .................................. 97 04118

[51] Int. Cl.[7] ............................. C07C 1/00; C07C 41/00; C07C 43/00
[52] U.S. Cl. ....................... 585/639; 585/640; 585/642; 568/697
[58] Field of Search ................................... 585/639, 640, 585/642; 568/697

[56] References Cited

U.S. PATENT DOCUMENTS

| 4,447,668 | 5/1984 | Smith, Jr. et al. ................. 585/639 |
| 5,354,831 | 10/1994 | Panster et al. ........................ 528/9 |
| 5,567,860 | 10/1996 | Mowry et al. ..................... 585/639 |

FOREIGN PATENT DOCUMENTS

| 0869107 | 10/1998 | European Pat. Off. . |
| 2 527 201 | 11/1983 | France . |
| 2669021 | 5/1992 | France . |

*Primary Examiner*—Hien Tran
*Assistant Examiner*—Thvan D. Dang
*Attorney, Agent, or Firm*—Millen, White, Zelano & Branigan, P.C.

[57] ABSTRACT

A process for producing an ether and an olefin from a hydrocarbon cut containing at least one tertiary olefin, by synthesis of at least one tertiary alkyl ether then fractionation to recover an organic fraction containing the ether which is decomposed into a product (P1) containing at least one alcohol and at least one tertiary olefin, which is fractionated, then the tertiary olefin is purified in a water washing extraction zone (L1) from which a fraction containing the tertiary olefin is recovered and sent to a separation zone (Co) from which an aqueous liquid fraction and a liquid hydrocarbon fraction containing the major portion of the tertiary olefin are recovered.

26 Claims, 2 Drawing Sheets

PROCESS FOR PRODUCING AN ETHER AND AN OLEFIN FROM A HYDROCARBON CUT CONTAINING AT LEAST ONE TERTIARY OLEFIN BY SYNTHESISING THEN DECOMPOSING AN ETHER, COMPRISING A FIRST STEP FOR PURIFYING THE OLEFIN BY FRACTIONATION

The invention concerns an integrated process for synthesising pure tertiary olefins from hydrocarbon cuts containing them, comprising a step for etherification of the hydrocarbon cut by at least one alcohol in which a product is formed which contains at least one tertiary alkyl ether which is then sent to a tertiary alkyl ether decomposition zone from which a product comprising at least one high purity tertiary olefin is recovered. In particular, it relates to a process for the production of very high purity isobutene from a $C_4$ hydrocarbon cut containing it, comprising formation, from this cut and methanol, of methyl-tertio-butyl-ether (MTBE), then decomposition of the MTBE and fractionation of the decomposition product to methyl alcohol and purified isobutene. The process of the present invention is also applicable to the synthesis of any tertiary olefin from a tertiary alkyl ether [for example ETBE (ethyl-tertio-butyl-ether), ETAE (tertio-amyl-methyl-ether), TAME (tertio-amyl-methyl-ether), and isopropyl-tertio-butyl-ether]. The remainder of the description of the present invention, in particular the operating conditions, is given by way of indication for the synthesis of isobutene from hydrocarbon cuts comprising essentially hydrocarbons containing 4 carbon atoms (among them isobutene) by synthesis and decomposition of MTBE.

A variety of routes for producing high purity isobutene can be employed industrially. The oldest is the sulphuric acid extraction process, but it is expensive and obsolete; it is known to be a contaminating process as waste acid is discharged. Further, the isobutene yield does not exceed 90%. The company ARCO uses tertio-butyl alcohol (TBA) dehydration, TBA being a by-product from their propylene oxide production process. The isobutane dehydrogenation process was developed during the last few years as a result of the large and increasing demand for MTBE. However, that process can only be profitable with very large production capacities.

High purity isobutene production from cracking MTBE is as suitable for small capacities as for large capacities. Further, such a route benefits from the infrastructure generated by the increasing importance of ethers in reformulated gasoline. A number of refineries throughout the world have MTBE production installations, for example. Further, there is a global exchange market for MTBE. This means that the production of high purity isobutene from MTBE can readily be carried out anywhere in the world, in and remote from refineries.

The concept of producing isobutene by decomposing an ether, more particularly MTBE, has long been known, but prior art processes have suffered from certain disadvantages.

In the process developed by SUNITOMO described, for example, in European patent application EP-A-0 068 785, the MTBE decomposition reaction is carried out in the liquid phase, in the presence of a solid acid catalyst which is an ion exchange resin. Two product streams are obtained: isobutene and methanol. As described, isobutene is obtained directly overhead from a distillation column with no other purification step. The isobutene obtained contains a certain number of impurities, beginning with a small fraction of methanol which is azeotropically distilled from dimethylether (DME), which is a volatile compound formed by condensing methanol in the presence of an acid catalyst. It is probable that the purity of the isobutene is insufficient for use in the production of polyisobutene or other copolymers. Further, there is no apparent way of avoiding the accumulation of heavy impurities such as dimers of isobutene or methyl sec-butyl ether (MSBE), which in the long run results in a fatal reduction of product purity.

In the process developed by ERDOLCHEMIE, described in U.S. Pat. No. 4,409,421, for example, isobutene is purified by eliminating residual alcohol entrained with the tertiary olefin by adsorption. This method has the disadvantage of requiring regular regeneration of the adsorbent. Further, the problem of recovery of the major portion of the alcohol from the decomposition step is not solved.

More recently in U.S. Pat. No. 5,095,164, the same company has described carrying out the decomposition reaction in a distillation apparatus. The catalyst is placed in the bottom of the column at the reboiler level. That particular implementation limits the reaction temperature, which is directly imposed by the nature of the ether and the operating pressure. Further, it apparently encourages the formation of reaction by-products such as the formation of dimers of isobutene and/or dimethylether formation. In this regard, the quality and/or development of the products is not clearly explained.

In U.S. Pat. No. 4,287,379, BASF describes a scheme which integrates both ether synthesis, its separation then the ether decomposition step to produce the isobutene. However, in order Lo avoid certain purification steps, etherification is carried out with a $C_3$ or $C_4$ alcohol, which is a major disadvantage as regards the international MTBE market.

This company has also described, in U.S. Pat. No. 4,320,232, a process for joint preparation of MTBE and isobutene comprising forming the ether from a $C_4$ Cut containing isobutene by reacting the cut with an alcohol mixture containing methanol and $C_3$ or $C_4$ alcohols during which a mixture containing MTBE and tertiary alkyl ethers of the $C_3$ and $C_4$ alcohols is formed which is separated into a fraction containing MTBE and a fraction containing the tertiary alkyl ethers of the $C_3$ and $C_4$ alcohols which is sent to a decomposition zone in which isobutene is formed. The use of an alcohol mixture considerably complicates the process particularly as regards separation and purification of the products. Further, that process usually necessitates the use of two etherification steps and an intermediate distillation step between those two steps.

Finally, we can also cite the two schemes of the SNAM-PROGETTI process presented in "Chemical Economy & Engineering Review", vol. 14, no 6, June 1982, including both the MTBE synthesis step and the MTBE decomposition step for the production of isobutene. It appears in those schemes that a certain loss of water by entrainment and/or saturation of the isobutene stream when washing the isobutene to eliminate alcohol is not taken into account. This can in the long run result in either a reduction in the washing water flow rate, or a loss of efficiency in the washing section. That could be deleterious to the quality of the isobutene produced. Further, in those schemes, all of the hydrocarbon fraction from the water extraction column which contains a relatively large quantity of free water is sent to the fractionation column to recover purified isobutene, which means that that column has to treat a large quantity of product and must therefore have large dimensions which renders the process particularly expensive and difficult to implement.

The process of the invention can overcome the disadvantages cited above. It concerns a process for the production of tertiary olefin(s) characterized by a (very) high purity, from a hydrocarbon cut containing it, by a method comprising forming then decomposing at least one tertiary alkyl ether. The process is thus also a process which is suitable for upgrading tertiary olefins contained in hydrocarbon cuts in the form of purified tertiary olefins, particularly for use in forming polymers and/or copolymers and/or in the form of tertiary alkyl ethers, particularly for use as additives for internal combustion engine fuels.

The invention concerns a process comprising forming then decomposing a tertiary alkyl ether as defined above, in particular MTBE or ETBE, to produce high purity tertiary olefin(s), in particular isobutene. When decomposing other ethers, a mixture can be obtained which contains a plurality of tertiary olefins. Thus in the case of TAME decomposition, a mixture containing 2-methyl-1-butene and 2-methyl-2-butene is obtained.

In addition to the reaction zone itself, the process of the invention comprises zones for purification, recovery or recycling the various products to optimise upgrading of the products used and to minimise losses.

The present invention concerns a process for the production of a pure tertiary olefin and/or a tertiary alkyl ether from a hydrocarbon cut containing at least one etherifiable tertiary olefin, the process comprising:
a) a step for forming at least one tertiary alkyl ether by bringing at least one hydrocarbon cut containing at least one etherifiable tertiary olefin into contact with at least one alcohol, generally a primary or secondary alcohol, preferably a primary alcohol generally containing 1 to 6, preferably 1 to 4, carbon atoms per molecule, preferably methyl alcohol or ethyl alcohol or isopropanol, more preferably methyl alcohol or ethyl alcohol, in a reaction zone generally comprising at least one reactor (R1) and containing an etherification catalyst;
b) a step for separating the major portion of the product from step a) into an organic fraction (O1) which is depleted in tertiary alkyl ether, preferably containing practically no tertiary alkyl ether, and an organic fraction (E1), enriched in the tertiary alkyl ether, preferably containing practically all of the tertiary alkyl ether formed during step a);
c) a step for decomposing at least a portion of the tertiary alkyl ether contained in the organic fraction (E1) from step b), in a reaction zone generally comprising at least one reactor (R2) containing a catalyst for decomposing said ether, into a product (P1) containing at least one alcohol and at least one tertiary olefin;
d) a step for fractionating at least a portion of product (P1), optionally all of the product, in a fractionation zone (C1) to obtain a fraction (A) containing the major portion of the tertiary olefin and possibly a minor fraction of the alcohol and possibly light compounds, initially contained in said portion of product (P1), and a fraction (B) containing the major portion of the alcohol formed in step c) and possibly ether which has not decomposed in step c);
e) a step for purifying at least a portion of fraction (A) in which said portion is sent to a water washing extraction zone (L1) from which an aqueous fraction (C) is obtained containing the major portion of the alcohol initially present in said portion and a fraction (D) is obtained containing the major portion of the tertiary olefin initially present in said portion, said fraction (D) containing said tertiary olefin, water, possibly light compounds and being substantially free of alcohol;
the process being characterized in that it comprises a step f) in which at least a portion of fraction (D) is sent to a separation zone (Co) from which an aqueous liquid fraction (Le) and an organic liquid fraction (Ohp1) containing the major portion of the tertiary olefin initially present in said portion of fraction (D) are recovered, said fraction (Ohp1) containing said tertiary olefin, a small quantity of water and possibly light compounds.

In a particular implementation of the process of the invention, a portion of the organic fraction (E1) containing the tertiary alkyl ether is sent for motor fuel pool and the other portion is sent to tertiary alkyl ether decomposition step c).

In a further particular implementation, the process of the invention comprises a step b1) in which at least a portion of the organic fraction (E1) from step b) containing the tertiary alkyl ether is sent to a purification zone (C4), for example by distillation, from which a heavy fraction (L1) which is depleted in tertiary alkyl ether, containing oligomers and MSBE (methyl sec-butyl ether), for example, is obtained, at least part of which can be flared off and/or at least part of which can be sent for motor spirit stock, and a lighter fraction (E2) which is enriched in tertiary alkyl ether, the major portion of which is sent to step c) for decomposition of said ether. In this implementation, a further portion of organic fraction (E1) containing the tertiary alkyl ether can be sent directly for motor spirit stock and a still further portion can be sent directly to step c). It is also possible to send all of the organic fraction (E1) containing the tertiary alkyl ether to zone (C4) of step b1). It is also possible to send only a portion of organic fraction (E1) to step b1) and all of the remainder directly to step c).

In a particular implementation of the process of the invention, which generally enables a high purity tertiary olefin to be obtained, at least a portion of the liquid fraction (Ohp1) recovered from step f) is sent in a step g) to a fractionation zone (C2) in which said portion of the liquid fraction (Ohp1) is fractionated into a fraction (Ohp2) containing the tertiary olefin and a fraction (F) containing the major portion of any light compounds and possibly a small quantity of residual water. Fraction (F) can be split into a gaseous fraction which is evacuated, for example flared off, and a liquid fraction at least part of which is returned to fractionation zone (C2) of step g) (line (20b) from line (20) or line (22) in FIGS. 1 and 2).

In this particular implementation, it is normally preferable that the fractionation zone of step g) comprises at least one means for recovering a substantially anhydrous light fraction from fraction (F). Usually, this means splits at least a portion of fraction (F) into a substantially anhydrous fraction and an aqueous fraction. This means is, for example, a separator drum provided with at least one means, for example a boot, for decanting and extracting an aqueous fraction. In this case, at least a portion of the aqueous fraction obtained from step g) is preferably recycled to step e) in water washing extraction zone (L1). The substantially anhydrous light fraction is then normally split into a gaseous fraction which is evacuated, for example flared off, and a substantially anhydrous liquid fraction at least a portion of which is returned to fractionation zone (C2) of step g). In a further implementation, at least a portion of fraction (F) (or the light fraction obtained from fraction (F)) from step g) is sent to a catalytic cracking zone. In a further variation, at least a portion of fraction (F) (or the light fraction obtained from fraction (F)) from step g) is sent to an ether synthesis reaction zone, preferably the ether synthesis reaction zone of step a). In yet another variation, at least a portion of fraction (F) (or the light fraction obtained from fraction (F)) from step g) is flared off.

Usually, the process of the present invention comprises a step h) in which at least a portion of the aqueous fraction (C)

from step e) is sent to a fractionation zone (C3) from which a fraction (G) containing the major portion of the alcohol initially present in said portion and an aqueous fraction (H) which is free of the major portion of the alcohol initially present in said portion are recovered. In this implementation, at least a portion of fraction (G) can be sent to an ether synthesis zone, preferably the ether synthesis reaction zone of step a). It is also possible to send all of the alcohol to the ether synthesis zone. Part or all of this alcohol can also be recovered for other uses. In this implementation, at least a portion of the aqueous fraction (H) obtained from step h) can also be recycled at least in part to step e) in water washing extraction zone (L1). In this implementation, at least a portion of the aqueous fraction (H) obtained from step f) can also be sent at least in part to a water treatment zone.

In a preferred implementation of the process of the present invention, at least a portion of fraction (B) obtained from step d) containing the major portion of the alcohol formed in step c) and possibly ether which has not been decomposed in step c) is sent to an ether synthesis zone, preferably to the ether synthesis zone of step a). It is also possible to send all of this fraction to the ether synthesis zone. Part or all of this fraction can also be recovered for other uses.

In a preferred implementation of the process of the present invention, at least a portion of the aqueous fraction (Le) obtained from step f) is recycled to step e) in water washing extraction zone (L1).

The various water recycling stages are independent of each other and can be carried out together or separately. Water which is not recycled is generally purged then normally sent to a waste water treatment zone. This purge usually occurs at least for the aqueous fraction (H) obtained from step h) when a zone (C3) is present. This purge can in particular prevent any accumulation of heavy compounds, for example heavy alcohols.

The conditions under which step a) of the present invention are carried out are conventional conditions which are well known to the skilled person for synthesising a tertiary alkyl ether from a hydrocarbon cut containing at least one tertiary olefin which is etherifiable by at least one alcohol, in particular an alcohol containing 1 to 6 carbon atoms per molecule, usually methanol or ethanol. The hydrocarbon cuts used in the context of the present invention contain at least one tertiary olefin and generally other saturated or unsaturated hydrocarbons such as other olefins, paraffins, possibly a small proportion of water, and/or oxides of carbon. The purified tertiary olefins which can be prepared using the present invention are compounds in which one carbon atom of the olefinic bond is branched. These compounds generally contain 4 to 10 carbon atoms per molecule, preferably 4 to 8 carbon atoms per molecule and usually 4 to 6 carbon atoms per molecule. Examples which can be cited are isobutene, 2-methyl-1-butene, 2-methyl-2-butene, tertiary hexenes, tertiary octenes and tertiary decenes. Examples which can be cited are $C_4$ and/or $C_5$ cuts from refining or from petrochemistry, such as $C_4$ and/or $C_5$ cuts from steam cracking, normally after diene extraction, $C_4$ and/or $C_5$ catalytic cracking cuts, cuts from isomerisation (hydroisomerisation or skeletal isomerisation) and cuts obtained by paraffin dehydrogenation. Ether synthesis is usually carried out in the presence of an acid catalyst, usually a solid acid catalyst selected from the group formed by organic acidic resins (for example sulphonic resins) and mineral acid resins which are generally solid under the ether synthesis reaction conditions (for example grafted mineral solids comprising at least one organic sulphonic group for example an alkylsulphonic, arylsulphonic, or alkylarylsulphonic group, in particular grafted polysiloxanes and more particularly those grafted with at least one alkylsulphonic group). The catalyst can be a commercial resin such as Amberlyst 15 or 35 resin or M31 resin from DOW-CHEMICAL, or a commercially available grafted polysiloxane. In step a), the quantity of alcohol used in normally such that the alcohol/tertiary olefin molar ratio present in the feed is about 0.5:1 to about 8:1, usually 0.8:1 to about 5:1, more usually about 0.9:1 to about 4:1. The reaction temperature is normally about 20° C. to about 120° C., usually about 30° C. to about 100° C., more usually about 40° C. to about 90° C. The HSV (hourly space velocity) as the volume of feed per volume of catalyst per hour is normally about 0.005 to about 100, usually about 0.01 to about 50 and more usually about 0.1 to about 10. The pressure is normally selected so that the constituents present in the reaction zone are in the liquid state. The absolute pressure in this etherification zone is about 1 bar to about 40 bar, normally about 1 bar to about 25 bar (1 bar equals 0.1 MPa).

The conditions for implementing step b) for separating the product from step a) into an organic fraction (O1) containing practically no tertiary alkyl ether and an organic fraction (E1) which is enriched in tertiary alkyl ether, preferably containing practically all of the tertiary alkyl ether formed during step a), are conventional conditions which depend on the compounds present in the product from step a). This separation can be carried out under conditions of varying severity to obtain a fraction (O1) still containing a small proportion of ether. The skilled person will be able to select the operating conditions to obtain the desired separation. The conditions are usually selected so as to obtain a fraction (E1) containing almost all of the ether formed during step a). Within the context of the invention, the etherification zone of step a) can be distinct from the separation or fractionation zone of step b), or an apparatus can be used which comprises a mixed reaction and fractionation zone (catalytic distillation column) such as that described in a number of prior art patents and other publications. In the case of a process in which MTBE is produced in step a), the distillation separation column normally operates at an absolute pressure of about 1 to about 30 bar, identical to or different from that prevailing in the etherification zone. This column normally to comprises 3 to 80 theoretical plates, usually 10 to 50 theoretical plates.

The conditions under which step c) of the present invention are carried out are conventional tertiary alkyl ether decomposition conditions which are well known to the skilled person. In a preferred implementation, this step c) is carried out without adding supplementary water to the product introduced into the decomposition zone. However, it is possible to add a certain quantity of water, for example up to the limit of the solubility of water in the ether which is to be decomposed. Normally, the conditions under which step c) is carried out are selected so that the major portion of the tertiary alkyl ether decomposes to produce an alcohol and a tertiary olefin. In this decomposition zone, the absolute pressure is normally about 1 to about 30 bars, preferably about 1 to about 12 bars, the temperature is normally in the range 50° C. to 300° C., preferably in the range 100° C. to 250° C., and the HSV (hourly space velocity) is normally in the range 0.1 to 200 $h^{-1}$, usually in the range 0.5 to 100 $h^{-1}$. In this zone, any of the acid catalysts known to the skilled person can be used. Solid acid catalysts are preferably used. Thus the catalyst can be selected from the group formed by organic acid resins and mineral acid resins which are generally solids under the ether decomposition reaction conditions. Of these compounds, those selected from the group formed by grafted mineral solids containing at least one alkylsulphonic, arylsulphonic or alkylarylsulphonic type organic group are usually used. In one preferred implementation of this step c), a catalyst selected from the group formed by polysiloxanes grafted with at least one alkylsulphonic group is used.

The general conditions for carrying out step d) for fractionation of product (P1) from ether decomposition step c) is a step in which the conditions are particularly selected as a function of the characteristics of the alcohol and tertiary olefin formed. The skilled person is able to select these conditions to obtain the desired separation between a fraction containing the major portion of the alcohol and a fraction containing the major portion of the olefin. Thus, for example, in the case of MTBE decomposition and formation of methanol and isobutene, the absolute pressure in the distillation column is about 1 to about 15 bar, preferably about 1 to about 10 bar, which may be identical to or different from that prevailing in the decomposition zone. The column bottom temperature depends both on the pressure prevailing in the column and the composition of the bottom product, in particular the molar ratio between the methanol and the MTBE which may be present following partial decomposition of this ether in step c). In the case of a unit treating 1 kg/h of MTBE, the distillation column normally comprises 3 to 80 theoretical plates, usually 10 to 50 theoretical plates.

In purification step e), at least a portion of fraction (A) containing the major portion of the tertiary olefin obtained from step c) is sent to a water washing extraction zone (L1). The quantity of water used for washing is normally such that the ratio between the volume of that quantity of water introduced into the extraction zone and that of the portion of product (A) introduced into the extraction zone ($V_{water}/V_A$) is about 0.005 to about 20. This quantity of water is usually such that the ratio $V_{water}/V_A$ is about 0.005 to 10, preferably about 0.01 to about 5, more preferably about 0.02 to about 1. The water flow rate in this washing zone (L1) is usually regulated so as to maintain a foundation level in the water and alcohol fractionation zone (C3) when such a zone (C3) is present. This foundation level can be defined as the minimum level required for the zone to operate properly. This parameter is a conventional parameter which is well known to the skilled person. The regulation is often carried out manually by the operators, but it is possible for this regulation to be carried out by an automatic Level Control Regulation circuit. Regardless of the selected mode of regulation, the quantity of water can generally be adjusted using a means for introducing makeup water into zone (L1). This makeup water can in particular compensate for loss of water due to entrainment of water and/or to saturation of the treated hydrocarbon stream and can replace any purged water. This extraction zone (L1) is normally a tray column which operates at a temperature of about 1° C. to about 100° C., preferably about 10° C. to about 60° C. The absolute pressure in this zone is about 1 to about 20 bars, normally about 1 to about 15 bars, identical to or different from that prevailing in the fractionation zone of step d).

Step f), which comprises a zone for separating at least a portion of fraction (D) from zone (L1) of step e) into an aqueous liquid fraction (Le) and a hydrocarbon liquid fraction (Ohp1) in a zone (Co), is a conventional step which is well known to the skilled person. This step is normally carried out in an apparatus termed a coalescer, in which water collects in the lower part of the apparatus by coalescence. The temperature and pressure conditions in this zone are in the same ranges as those prevailing in zone (L1). The pressure (or respectively the temperature) can be identical to or different from that in zone (L1). In zone (Co), the free water contained in the product (D) from step e) is separated out. Further, this zone (Co) also usually acts as a feed drum for the tertiary olefin purification zone (C2) when such a zone (C2) is present. Any other means known to the skilled person can be used in the present invention. As an example, an absorbent with preferential selectivity for the aqueous or organic fraction could be used.

Optional step g) for fractionation in a zone (C2) of at least a portion of the fraction (Ohp1) from zone (Co) of step f) into a fraction (Ohp2) containing the tertiary olefin and a fraction (F) containing the major portion of light compounds which may be present in fraction (Ohp1) and possibly residual water contained in the portion of the liquid fraction (Ohp1), is normally carried out in a distillation column operating at an absolute pressure of about 1 to about 15 bar, usually about 3 to about 10 bar, identical to or different from that prevailing in the separation zone of step f). for a unit producing 0.6 kg/h of isobutene, this column normally has about 3 to about 80 theoretical plates, usually about 5 to about 50 theoretical plates. The column bottom temperature mainly depends on the pressure prevailing in the column.

Step h) for fractionating, in a zone (C3), at least a portion of aqueous fraction (C), containing the major portion of the alcohol initially present in fraction (A), into a fraction (G) containing the major portion of the alcohol initially present in fraction (C) and an aqueous fraction (H) which is free of the major portion of the alcohol initially present in fraction (C), is normally carried out in a distillation column (C3) at an absolute pressure of about 1 to about 12 bars, preferably about 1 to about 8 bars, identical to or different from that prevailing in water washing extraction zone (L1) of step e). The column bottom temperature particularly depends on the pressure prevailing in that column and is normally about 50° C. to about 300° C., usually about 65° C. to about 200° C. The column normally comprises 2 to 80 theoretical plates, usually 3 to 60 theoretical plates.

Figure 1:
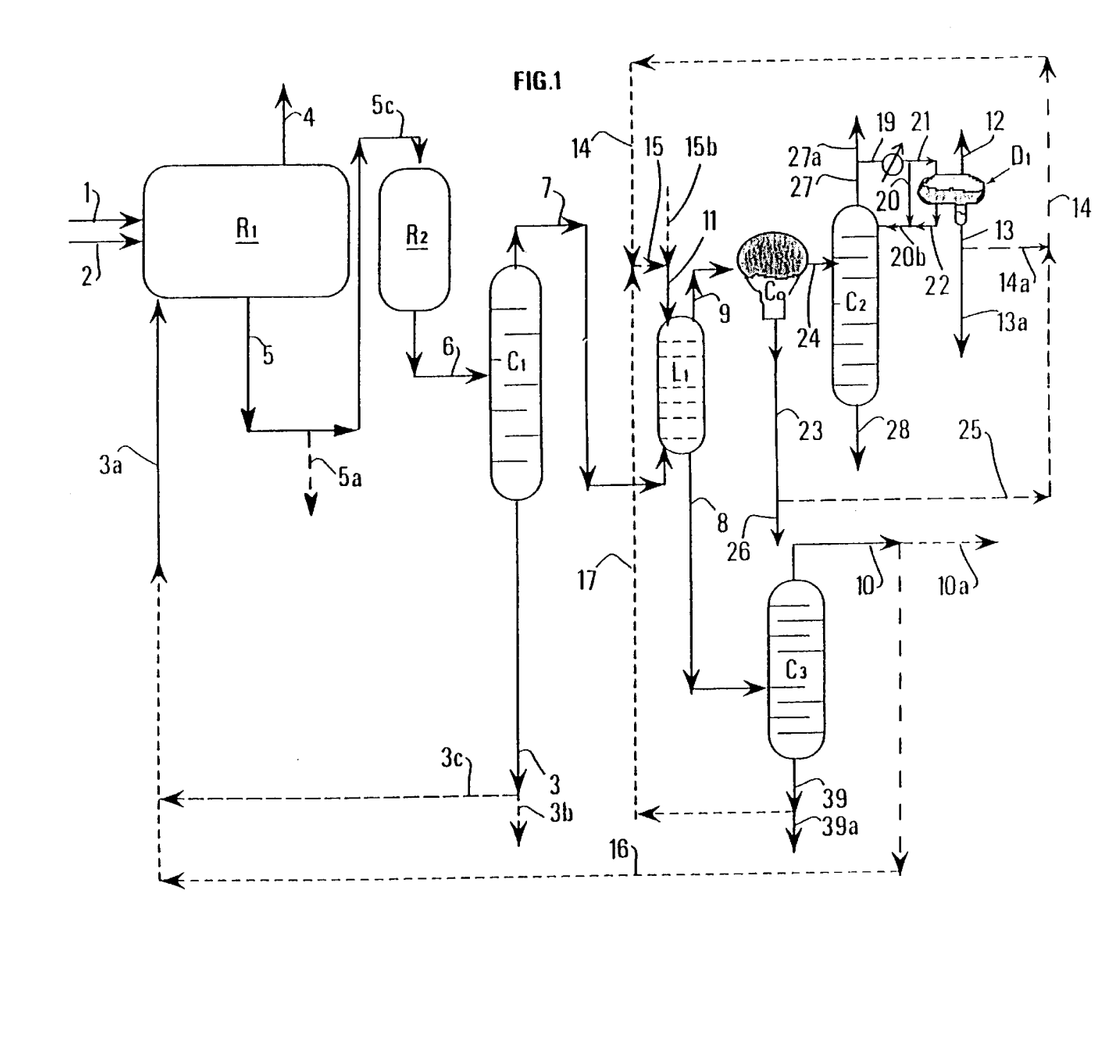
FIGS. 1 and 2 are flowcharts each illustrating a preferred variation of an implementation of the process of the present invention. The dotted lines show the various possible options.

In the first variation shown in FIG. 1, the hydrocarbon feed containing at least one tertiary olefin is introduced into etherification and fractionation zone (R1) via line 1. An alcohol makeup is also introduced into this zone (R1) via line 2 and any recycled alcohol is introduced via line 3a. Zone (R1) contains an acid etherification catalyst. The product obtained by etherification of the hydrocarbon cut is split in zone (R1) into an organic hydrocarbon fraction (O1) which leaves via line 4 and an organic fraction (E1) containing the ether formed which leaves via line 5. A portion of this organic fraction (F1) is sent for motor spirit stock via line 5a and the other portion is sent to ether decomposition zone (R2) via line 5c. A product (P1) containing a tertiary olefin and an alcohol is recovered via line 6 and sent to a fractionation column (C1). The product containing the alcohol leaving column (C1) via line 3 can, for example, be sent to zone (R1) in part via lines 3, 3c then 3a. A further portion of this product can be evacuated via lines 3 and 3b. The product containing the tertiary olefin is introduced via line 7 into water washing extraction zone (L1) into which water is introduced via line 11 and from which a fraction (D) which is depleted in alcohol is recovered via line 9 and sent to separation zone (Co) from which an aqueous liquid fraction (Le) is recovered via line 23 and a hydrocarbon liquid fraction (Ohp1) containing the major portion of the tertiary olefin initially present in fraction (D) is recovered via line 24. Fraction (Ohp1), containing the tertiary olefin, a small quantity of water and possibly light compounds, is sent to a fractionation zone (C2) via line 24. An aqueous product (2) containing alcohol is recovered from the outlet from zone (L1) via line 8 and introduced into fractionation zone (C3). Ultra pure tertiary olefin (Ohp2) is recovered from the fractionation zone (C2) via line 28 and light products are recovered via line 27. Part of the light products are, for example, flared off via line 27 and 27a, but they can also be sent to a catalytic cracking zone or to an ether synthesis zone, preferably zone (R1), and they can also be recycled to fractionation zone (C2) as a reflux via lines 19, 20 and 20b. It is also possible, and this is a preferred implementation, to sent at least a portion of these light products to a separation zone (D1) via lines 19 and 21, from which a fraction a major portion of which is constituted by water is recovered via line 13 and a liquid fraction of light products is recovered via line 22 and sent via line 20b as a reflux to column (C2), and at least a portion of the gaseous light products are recovered to via line 12 and at least partially flared off, for example, but which can also be sent to a catalytic cracking zone or to an ether synthesis zone, preferably zone (R1). It is also possible to combine the two embodiments described above. Part of the aqueous fraction recovered via line 13, for example, can be returned to zone (L1) via lines 14a, 14, 15 and 11 or recovered in part via line 13a. Alcohol is recovered from fractionation zone (C3) via line 10, part of which can, for example, be sent to zone (R1) via lines 16 and 3a or it can be recovered via line 10a. From this zone (C3), an aqueous fraction is also recovered via line 39 which can be sent at least in part to a water treatment zone via line 39a or recycled at least in part to zone (L1) via lines 17, 15 and 11. At least part of the aqueous liquid fraction (Le) recovered from separation zone (Co) via line 23 can be sent to a water treatment zone via line 26 or recycled at least in part to zone (L1) via lines 25, 14, 15 and 11, in addition to a possible external makeup of water via line 15b.

Figure 2:
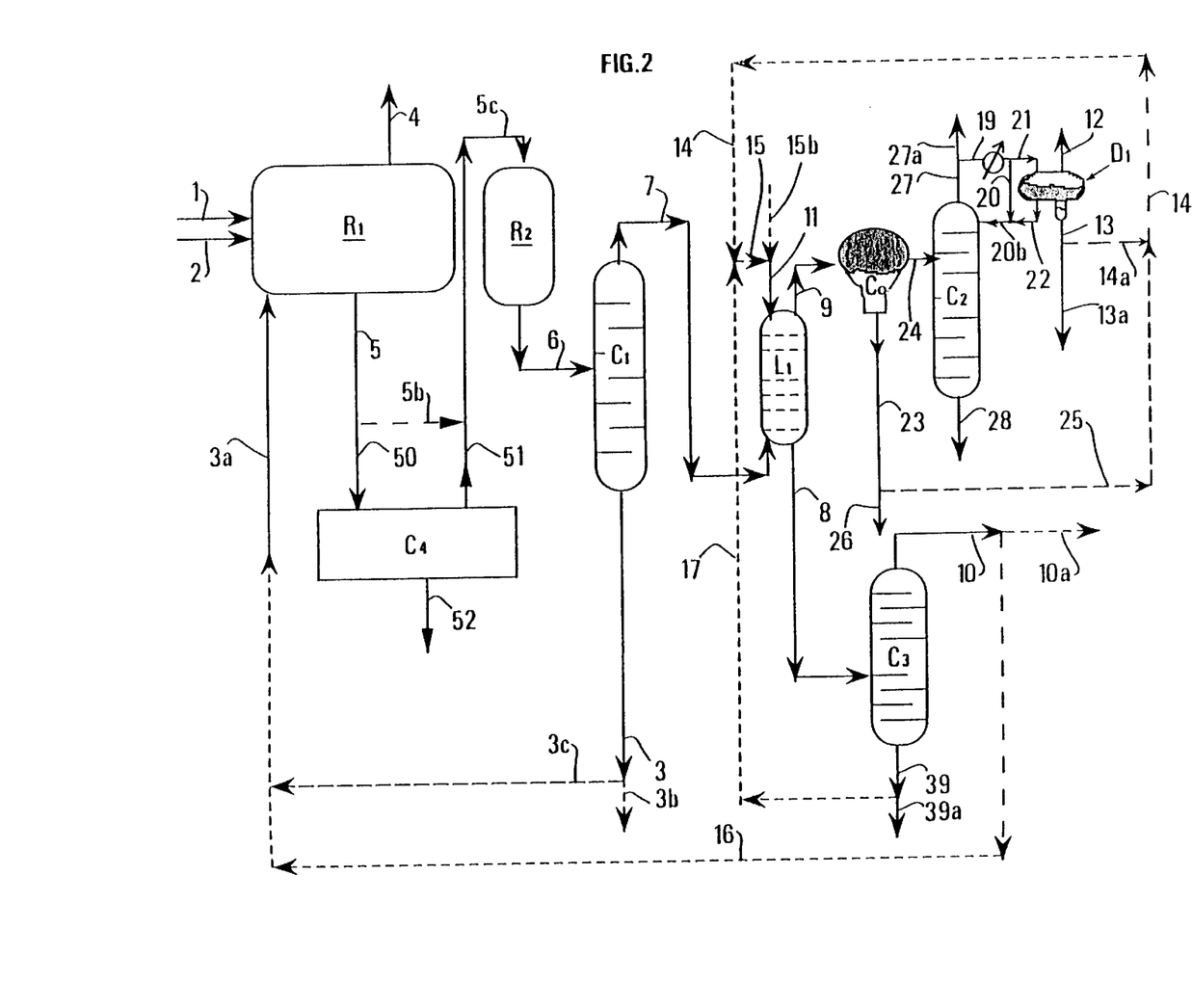

The second variation shown in FIG. 2 differs from that described for FIG. 1 in that at least part of product (E1) leaving the etherification zone and (R1) is sent via lines 5 and 50 to a purification zone (C4), the other portion, if there is one, being sent directly to ether decomposition zone (R2) via lines 5, 5b and 5c. A heavy fraction which is depleted in ether is recovered from purification zone (C4) via line 52 and a fraction which is enriched in ether is recovered via line 51 and sent to zone (R2) via line 5c. The other elements shown in FIG. 2 are similar to those described in connection with FIG. 1. At least part of the heavy fraction recovered via line 52 is, for example, sent for fuel stock.

The following examples illustrate the invention without limiting its scope.

EXAMPLE 1

A pilot type unit was used which comprised two tube reactors (R1) and (R2), with 20 milliliter and 10 milliliter volumes respectively. The first reactor (R1) contained 6 grams of Amberlyst 15 resin sold by ROHM & HAAS and operated at a relative pressure of 10 bar, at an average temperature of 50° C. It was supplied with a $C_4$ cut from catalytic cracking containing 20% by weight of isobutene and by pure methanol sold by ALDRICH as a product with a purity of over 99% by weight. The quantity of methanol was adjusted so that the methanol/isobutene molar ratio introduced into reactor (R1) was 1.2. The reactor operated at an HSV of 0.5 $h^{-1}$. Under the selected conditions, conversion of isobutene to MTBE was 97.5%.

The second reactor (R2) contained 3 grams of commercially available catalyst based on polysiloxanes grafted with at least one alkylsulphonic group. Reactor (R2) was supplied with a feed containing 100% by weight of MTBE, at an HSV of 15 $h^{-1}$, the relative pressure in the reactor was 7 bar and the average temperature was 160° C. Table 1 shows the composition of the feed introduced into MTBE decomposition reactor (R2) and the composition of the product recovered from the outlet from reactor (R2).

TABLE 1

|  | Feed (wt %) | R2 effluent (wt %) |
|---|---|---|
| MTBE | 100 | 10 |
| Isobutene |  | 56.1 |
| Methanol |  | 32.1 |
| DME |  | 0.5 |
| Dimers |  | 1.1 |
| $H_2O$ |  | 0.2 |

The various purification sections were calculated using software produced by American company SIMSCI (SIMulation SCIence INC.) under the trade name Pro II.

A distillation column (Co1), operating at a relative pressure of 7 bar, comprising 10 theoretical plates, was used in step b) of the process of the invention to obtain a bottoms product (E1) and an overhead product (O1). (This simulated fractionation of the product from step a) for etherification of the isobutene contained in the $C_4$ cut).

A distillation column (C1), operating at a relative pressure of 7 bar, comprising 10 theoretical plates, was used in step c) of the process of the invention to obtain a bottoms product (B) and an overhead product (A). (This simulated fractionation of the product from MTBE decomposition step c).

A water washing extraction column (L1), a tray column operating at a temperature of 30° C. and a relative pressure of 12 bars, was used in step e) of the process of the invention to obtain an aqueous fraction (C) and an organic fraction (D).

A coalescer type (Co) system for extracting free water entrained in step e) in fraction (D), enabled an aqueous fraction (Le) and an organic fraction (Ohp1) to be obtained. It operated at a relative pressure of 12 bar and a temperature of 30° C.

A distillation column (C2), the last step in the isobutene purification, operating at a relative pressure of 7 bars and comprising 10 theoretical plates, was used in step g) of the process of the invention to obtain a bottoms product (Ohp2) which was purified isobutene and an overhead product (F) containing light compounds.

Column (Co1) was supplied with the product from the etherification reactor. Product (E1) recovered from the bottom of column (Co1) was used to supply reactor (R2). Column (C1) was supplied with effluent from (R2). Product (A) recovered overhead from (C1) was sent to extraction column (L1) where it was washed with a quantity of water the volume flow rate of which was a tenth of the flow rate of (A). An aqueous fraction (C) containing the major portion of the methanol contained in (A) and a hydrocarbon fraction (D) containing a small quantity of entrained free water were recovered. This fraction of free water was then eliminated after decanting in a decanting system (Co) in the form of a fraction (Le) and a hydrocarbon organic fraction (Ohp1). Finally, the hydrocarbon fraction (Ohp1) was treated in column (C2) to produce a column bottoms fraction (Ohp2) which was high purity isobutene and a light overhead fraction (F) containing dimethylether (DME) in particular.

The material balances are given in Tables 2, 3 and 4 below.

TABLE 2

|  | Feed R1 (weight) | Effluent R1 (weight) | Col head (weight) | Col bottom (weight) |
|---|---|---|---|---|
| Isobutene | 20 | 0.6 | 0.6 |  |
| C4 ex isobutene | 80 | 80 | 80 |  |
| Methanol | 13.7 | 2.7 | 2.7 |  |
| MTBE | 0 | 30.4 | 0 | 30.4 |
| Total | 113.7 | 113.7 | 83.3 | 30.4 |

TABLE 3

|  | Effluent R2 (wt %) | Product B column C1 (g/h) | Product A column C1 (g/h) | Washing water column L1 | Fraction C column L1 | fraction D column L1 |
|---|---|---|---|---|---|---|
| MTBE | 10 | 10 |  |  |  |  |
| Isobutene | 56.1 |  | 56.1 |  |  | 56.1 |
| Methanol | 32.1 | 30.4 | 1.7 |  | 1.7 | — |
| DME | 0.5 |  | 0.5 |  |  | 0.5 |
| Dimers | 1.1 | 1.1 |  |  |  | — |
| H$_2$O | 0.2 |  | 0.2 | 10 | 9.2 | 1 |
| Flow rate (g/h) | 100 | 41.5 | 58.5 | 10 | 10.9 | 57.6 |

TABLE 4

|  | Aqueous fraction Le extracted by Co | Organic fraction Ohp1 Co outlet | Fraction F column C2 | Fraction Ohp2 column C2 |
|---|---|---|---|---|
| Isobutene |  | 56.1 | 1.72 | 54.38 |
| DME |  | 0.5 | 0.49 | 0.01 |
| H$_2$O | 0.99 | 0.01 | 0.01 |  |
| Flow rate (g/h) | 0.99 | 56.61 | 2.22 | 54.39 |
| Isobutene purity (%) |  |  |  | 99.98% |

This example shows that carrying out the process of the invention can produce, from a C$_4$ cut containing isobutene, an isobutene in a purity of 99.98% with an overall conversion of 82.6%. Conversion can be improved by using a variety of recycling stages, namely of unconverted alcohol, and by purging a portion of the ether formed during etherification to gasoline fractions. Conversion can then exceed 94%.

EXAMPLE 2

A pilot type apparatus comprising a tube reactor R1 and R2 was used to carry out the two reaction steps, synthesis and decomposition of the ether TAME. The distillation separation steps and the purification sections were calculated using Pro II software.

In the pilot unit, the ether TAME was synthesised by reacting isoamylenes with methanol in the presence of Amberlyst 15 resin (produced by ROHM & HAAS). An FCC type C$_5$ cut containing 22% by weight of isoamylenes (2-methyl-1-butene and 2-methyl-2-butene) with added methanol (Aldrich, purity >99% by weight) were used to provide a feed with a methanol/isoamylene stoichiometry of 1. The unit provided with reactor R1 was operated at 10 bars (relative pressure) and 60° C., at an HSV of 0.5 h$^{-1}$. During this step, the conversion of isoamylenes to TAME rose to 67%.

The pilot unit was then operated under different operating conditions to carry out the reverse TATME decomposition reaction. Reactor R2 contained Deloxan ASP catalyst (produced by DEGUSSA). The unit was operated at a relative pressure of 7 bar, at an average temperature of 140° C. Reactor R2 was supplied with a feed containing 100% by weight of TAME, at an HSV of 6 h$^{-1}$. The product recovered from the outlet from reactor R2 had the composition given in Table 5:

TABLE 5

TAME decomposition reaction section

|  | Feed (wt %) | Effluent R2 (wt %) |
|---|---|---|
| TAME | 100 | 15 |
| Isoamylenes |  | 58.2 |
| Methanol |  | 26.45 |
| DME |  | 0.25 |
| Dimers |  | 0.1 |

As in the preceding example, the various purification sections were calculated using Pro II software

TABLE 6

Material balance relative to TAME synthesis

|  | Feed R1 (weight) | Effluent R1 weight) | Overhead C1 (weight) | Bottom C1 (weight) |
|---|---|---|---|---|
| Isoamylenes | 22 | 7.26 | 7.26 |  |
| C5 ex isoamylenes * | 78 | 78 | 78 |  |
| Methanol | 10.1 | 3.36 | 3.36 |  |
| TAME | 0 | 21.48 |  | 21.48 |
| Total | 110.1 | 110.1 | 88.62 | 21.48 |

* This includes 3-methyl-1-butene, an olefin classified as "non-etherifiable".

TABLE 7

Material balance relating to decomposition of TAME and production of high purity isoamylenes

|  | Effluent R2 (wt %) | Bottom C2 (g/h) | Head C2 or product A | Washing water | Fraction C | Fraction D |
|---|---|---|---|---|---|---|
| TAME | 15 | 15 |  |  |  |  |
| Isoamylenes | 58.2 |  | 58.2 |  |  | 58.2 |
| Methanol | 26.45 | 24.45 | 2 |  | 2 |  |
| DME | 0.25 |  | 0.25 |  |  | 0.25 |
| Dimers | 0.1 | 0.1 |  |  |  |  |
| H$_2$O |  |  |  | 12 | 11.5 | 0.5 |
| Flow rate (g/h) | 100 | 39.55 | 60.45 | 12 | 13.5 | 58.95 |

Integration of the two processes (TAME synthesis then TAME decomposition) allowed isoamylenes (2-methyl-1-butene and 2-methyl-2-butene) to be extracted from a C$_5$ cut with a minimum yield of 56% (the yield could be improved by recycling unconverted ether) and with a purity of over 98%.

What is claimed is:

1. A process for the production of a pure tertiary olefin and/or a tertiary alkyl ether from a hydrocarbon cut containing at least one etherifiable tertiary olefin, the process comprising:
   a) a step for forming at least one tertiary alkyl ether by bringing at least one hydrocarbon cut containing at least one etherifiable tertiary olefin into contact with at least one alcohol in a reaction zone (R1) containing an etherification catalyst;
   b) a step for separating the major portion of the product from step a) into an organic fraction (O1) which is depleted in tertiary alkyl ether and an organic fraction (E1) which is enriched in the tertiary alkyl ether formed during step a);
   c) a step for decomposing at least a portion of the tertiary alkyl ether contained in the organic fraction (E1) from step b), in a reaction zone (R2) containing a catalyst for decomposing said ether, into a product (P1) containing at least one alcohol and at least one tertiary olefin;
   d) a step for fractionating at least a portion of product (P1) in a fractionation zone (C1) to obtain a fraction (A) containing the major portion of the tertiary olefin and optionally a minor fraction of the alcohol and optionally light compounds, initially contained in said portion of product (P1), and a fraction (B) containing the major portion of the alcohol formed in step c) and optionally ether which has not decomposed in step c);
   e) a step for purifying at least a portion of fraction (A) in which said portion is sent to a water washing extraction zone (L1) from which an aqueous fraction (C) is obtained containing the major portion of the alcohol initially present in said portion and a fraction (D) is obtained containing the major portion of the tertiary olefin initially present in said portion, said fraction (D) containing said tertiary olefin, water, optionally light compounds and being substantially free of alcohol;
said process being characterized in that it comprises a step f) in which at least a portion of fraction (D) is sent to a separation zone (Co) from which an aqueous liquid fraction (Le) and an organic liquid fraction (Ohp1) containing the major portion of the tertiary olefin initially present in said portion of fraction (D) are recovered, said fraction (Ohp1) containing said tertiary olefin, a small quantity of water and optionally light compounds.

2. A process according to claim 1, in which a portion of the organic fraction (E1) containing tertiary alkyl ether is passed to a motor fuel pool and the other portion is sent to tertiary alkyl ether decomposition step c).

3. A process according to claim 1, comprising a step b1) in which at least a portion of the organic fraction (E1) from step b) containing the tertiary alkyl ether is sent to a purification zone (C4) from which a heavy fraction (L1) which is depleted in tertiary alkyl ether is obtained, also a lighter fraction (E2) which is enriched in tertiary alkyl ether is obtained which is sent to step c) for decomposing said ether.

4. A process according to claim 1, in which at least a portion of the liquid fraction (Ohp1) recovered from step f) is sent in a step a) to a fractionation zone (C2) in which said portion of the liquid fraction (Ohp1) is fractionated into a fraction (Ohp2) containing the tertiary olefin and an overhead a fraction (F) containing the major portion of any light compounds and a small quantity of residual water.

5. A process according to claim 4, further comprising in step g) condensing fraction (F) so as to produce a condensate comprising a substantially anhydrous light fraction and an aqueous fraction.

6. A process according to claim 5, further comprising in step g) decanting and extracting an aqueous fraction.

7. A process according to claim 6, in which the aqueous fraction obtained in step g) is recycled at least in part to step e) in water washing extraction zone (L1).

8. A process according to claim 4, in which at least a portion of fraction (F) or the substantially anhydrous light fraction obtained in step g) from said fraction (F) is sent at least in part to a catalytic cracking zone.

9. A process according to claim 4, in which at least a portion of fraction (F) or the substantially anhydrous light fraction obtained in step g ) from said fraction (F) is sent at least in part to the ether synthesis zone (R1) of step a).

10. A process according to claim 1 further, comprising a step h) in which at least a portion of the fraction (C) from step e) is sent to a fractionation zone (C3) from which a fraction (G) containing the major portion of the alcohol initially present in said portion and an aqueous fraction (H) which is free of the major portion of the alcohol initially present in said portion are recovered.

11. A process according to claim 10, in which at least a portion of fraction (G) obtained from step h) containing alcohol is sent to the ether synthesis zone (R1) of step a).

12. A process according to claim 10, in which at least a portion of the aqueous fraction (H) obtained from step h) is sent at least in part to a water treatment zone.

13. A process according to claim 10, in which at least a portion of fraction (H) obtained from step h) is recycled at least in part to step e) of water washing extraction zone (L1).

14. A process according to claim 1, in which at least a portion of fraction (B) obtained from step d) containing alcohol is sent to the ether synthesis zone (R1) of step a).

15. A process according to claim 1, in which at least a portion of the aqueous fraction (Le) obtained from step f) is recycled at least in part to step e) in water washing extraction zone (L1).

16. A process according to claim 1, in which in step e) for purifying at least a portion of fraction (A), a quantity of water is introduced into water washing extraction zone (L1) such that the volume ratio between the volume of said quantity of water introduced into said extraction zone and that of said portion of fraction (A) introduced into said extraction zone ($V_{water}/V_A$) is 0.005 to 20.

17. A process according to claim 1, in which the water washing extraction zone (L1) of step e) further comprises introducing makeup water.

18. A process according to claim 1, in which the tertiary alkyl ether synthesis catalyst is selected from the group consisting of organic acid resins and mineral acid resins.

19. A process according to claim 1, in which the tertiary alkyl ether decomposition catalyst is selected from the group consisting of organic acid resins and mineral acid resins.

20. A process according to claim 1, in which the tertiary alkyl ether decomposition catalyst is selected from the group consisting of grafted mineral solids comprising at least one organic alkylsulphonic, arylsulphonic or alkylarylsulphonic group.

21. A process according to claim 1, in which the tertiary alkyl ether decomposition catalyst is selected from the group consisting of polysiloxanes grafted with at least one alkylsulphonic group.

22. A process according to claim 13, in which at least a portion of the aqueous fraction (Le) obtained from step f) is recycled at least in part to step e) in water washing extraction zone (L1).

23. A process according to claim 22, in which the aqueous fraction obtained in step g) is recycled at least in part to step e) in water washing extraction zone (L1).

24. A process according to claim 11, in which at least a portion of fraction (B) obtained from step d) containing alcohol is sent to the ether synthesis zone (R1) of step a).

25. A process according to claim 13, in which at least a portion of fraction (H) obtained from step h) is recycled at least in part to step e) of water washing extraction zone (L1).

26. A process according to claim 24, in which at least a portion of the aqueous fraction (Le) obtained from step f) is recycled at least in part to step e) in water washing extraction zone (L1).

* * * * *